United States Patent [19]

Raz

[11] Patent Number: 5,535,751
[45] Date of Patent: Jul. 16, 1996

[54] CONFOCAL ULTRASONIC IMAGING SYSTEM

[75] Inventor: Ryan S. Raz, Toronto, Canada

[73] Assignee: Morphometrix Technologies Inc., Toronto, Canada

[21] Appl. No.: 361,605

[22] Filed: Dec. 22, 1994

[51] Int. Cl.$^6$ ..................................................... A61B 8/00
[52] U.S. Cl. ..................................... 128/663.01; 128/916
[58] Field of Search ........................ 128/660.07, 660.08, 128/660.09, 660.10, 661.01, 916, 663.01; 73/625, 626

[56] References Cited

U.S. PATENT DOCUMENTS

| | | | |
|---|---|---|---|
| 4,227,417 | 10/1980 | Glenn | 73/625 |
| 4,850,363 | 7/1989 | Yanagawa | 128/660.09 |
| 5,088,496 | 2/1992 | Bernard | 128/661.01 |

FOREIGN PATENT DOCUMENTS 0012262  6/1980  European Pat. Off. .

*Primary Examiner*—George Manuel
*Attorney, Agent, or Firm*—Ridout & Maybee

[57] ABSTRACT

An ultrasonic imaging system incorporates an imaging device utilizing confocal acoustic focusing of ultrasonic transducers together with apparatus for moving points of focus of the transducers to scan a volume to be imaged and gather data as to the acoustic reflectivity of matter within the volume, the gathered data being used to construct an image of the volume. In a preferred arrangement the point of focus of each transducer is moved in three dimensions. Use of confocal techniques can permit enhanced resolution to be obtained compared with conventional ultrasonic imaging techniques.

8 Claims, 3 Drawing Sheets

CONFOCAL ULTRASONIC IMAGING SYSTEM

FIELD OF THE INVENTION

This invention relates to ultrasonic imaging systems, particularly systems for three-dimensional imaging of soft tissue such as breast, muscle and joint tissue.

BACKGROUND OF THE INVENTION

Existing ultrasonic imaging systems have limitations upon resolution that restrict their usefulness in identifying fine detail. These limitations arise both from limited axial resolution on the Z (depth) axis due to focusing limitations, and lateral resolution on the X and Y axes due to limitations upon the number of elements it is feasible to include in an array of imaging transducers, or the rate at which such transducers can be scanned. Axial resolution limitations can to some extent be bypassed by temporal filtering based on transit time, but lateral resolution restrictions have proved more intractable.

It is an object of the present invention to provide an ultrasonic imaging system which addresses these problems.

SUMMARY OF THE INVENTION

According to the invention in its broadest aspect an ultrasonic imaging device comprises at least one acoustic transducer associated with a confocal acoustic focusing system and means to move the point of focus of each such focusing system progressively to different coordinates within an acoustically transmissive volume to be imaged to gather data as to the acoustic reflectivity of matter within said volume at said different coordinates, and means to construct an image or images of the volume from said data. Preferably multiple transducers and associated confocal focusing systems are disposed in an array.

By a confocal acoustic scanning focusing system is meant a device analogous to the optical system of an optical confocal microscope but utilizing acoustic rather than optical energy.

Preferably multiple transducers and their focusing systems are arranged in a two dimensional array, and are movable in two dimensions in the plane of that array so as to scan their points of focus in a plane within said volume parallel to the array, and their points of focus are also movable orthogonally to the array, to scan parallel planes within said volume. Preferably also the transducers act sequentially both to transmit and receive acoustic energy through their associated focusing systems.

Further features of the invention will become apparent from the appended claims and following description with reference to the accompanying drawings.

IN THE DRAWINGS

DESCRIPTION OF THE PREFERRED EMBODIMENT

Figure 1:
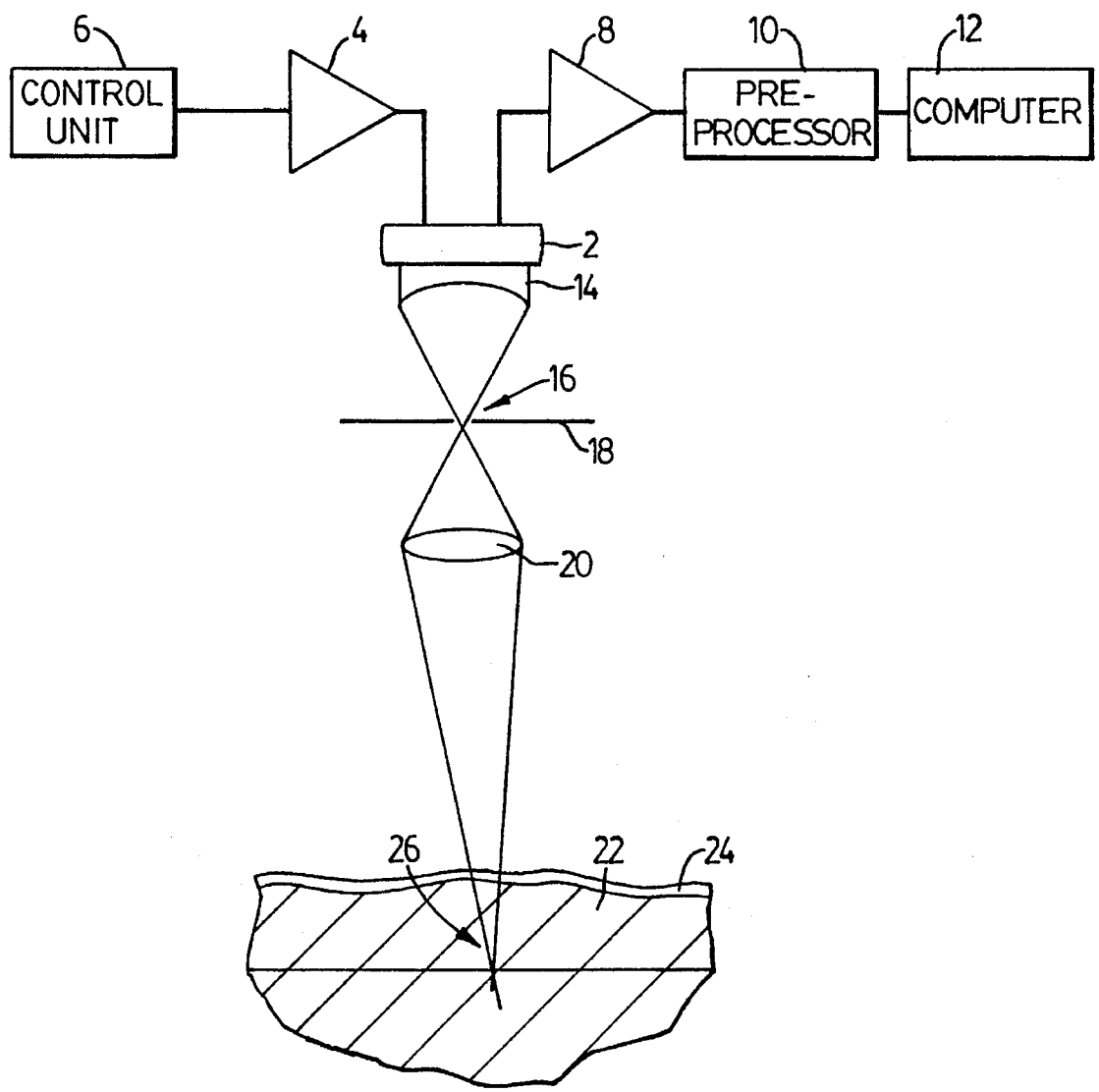
FIG. 1 shows diagrammatically a single confocal acoustic scanning device.

Referring first to FIG. 1, an acoustic transducer 2 acts alternately as both an acoustic transmitter, transducing into acoustic energy pulses of high frequency electrical energy from a driver 4 under control of a control unit 6, and an acoustic receiver, receiving reflected acoustic energy at the same frequency and transducing it to electrical energy, which is preamplified in a preamplifier 8 and passed via an analog signal preprocessor 10 to a signal processing computer 12. The transducer is associated with a first acoustic lens 14, which may be integral with the transducer if the latter has an appropriately formed radiating surface, which lens focuses energy from the transducer on a small aperture or pin-hole 16 in an aperture plate 18. Acoustic energy emerging from the pin-hole is focused by a second lens 20 to form an image of the pinhole at a focal point 26 in a focal plane within an acoustically transmissive body 22, typically soft tissue as mentioned above. The body 22 may be matched acoustically to a medium such as water or other liquid or gaseous medium within which the remainder of the acoustic system is located, by a coupling layer or membrane 24. Assuming that the lens 20 has a large aperture, that the pin-hole is very small, that the performance of the lens is good, and that the frequency of the acoustic energy is high enough that its wavelength is very small relative to the optical dimensions of the components of the system, acoustic energy from the transducer will have a sharp intensity peak at the focal point with good lateral and depth resolution, and equally, energy reflected from that point will be focused by the lens 20 on the pin-hole 16, with a high degree of rejection of acoustic energy reflected from elsewhere within the body 22. Reflected acoustic energy passing through the pin-hole and the lens 14, and received by the transducer, is therefore proportional to the reflectivity of the body 22 at the location of the focal point, and the intensity of echo signals from the preamplifier 8 resulting from a series of pulses applied by the driver 4 will vary according with the acoustic reflectivity of the body 22 as the focal point 26 is moved relative to the body, for example by moving the scanning device as a whole.

The device shown in FIG. 2 consists of a planar array 30 of confocal systems as described with reference to FIG. 1, mounted within a housing 31 for motion in three-dimensions within the housing under control of actuators 33, 35 and 37 powered by electrical driver circuits 39. The acoustic transmission medium within the housing is acoustically coupled to the body 22, for example human tissue to be imaged, through the coupling layer 24 in the form of a flexible membrane. The scanning array comprises a set of systems comprising acoustic transducers 2 and confocal focusing systems having lenses 14 and 20, and pin-holes 16, the components being arranged in planar lattices. The focusing systems in the array 30 have focal points 26 in an image plane 32 which is a precise distance from the array 30. The scanning device elements in the planar array are identical and define an image plane within the body 22.

The use of ultrasonic acoustic energy in such a confocal system can allow a substantial improvement of both the lateral and axial resolution of an ultrasonic imaging instrument. By overcoming the resolution limits of conventional ultrasonic systems the confocal arrangement is capable of lateral precision comparable to standard X-ray techniques and improves upon their axial resolution, but does not make use of ionizing radiation. Moreover, the complete instrument does not require the large magnetic fields of associated magnetic resonance imaging (MRI) nor the shielding safeguards of X-ray examinations, and so offers advantages in both cost and convenience for clinical tomographic imaging. Furthermore, the arrangement is well adapted to exploit modern piezoelectric plastics along with surface mount and photolithographic fabrication techniques to provide a compact and economically manufactured instrument.

Figure 2:
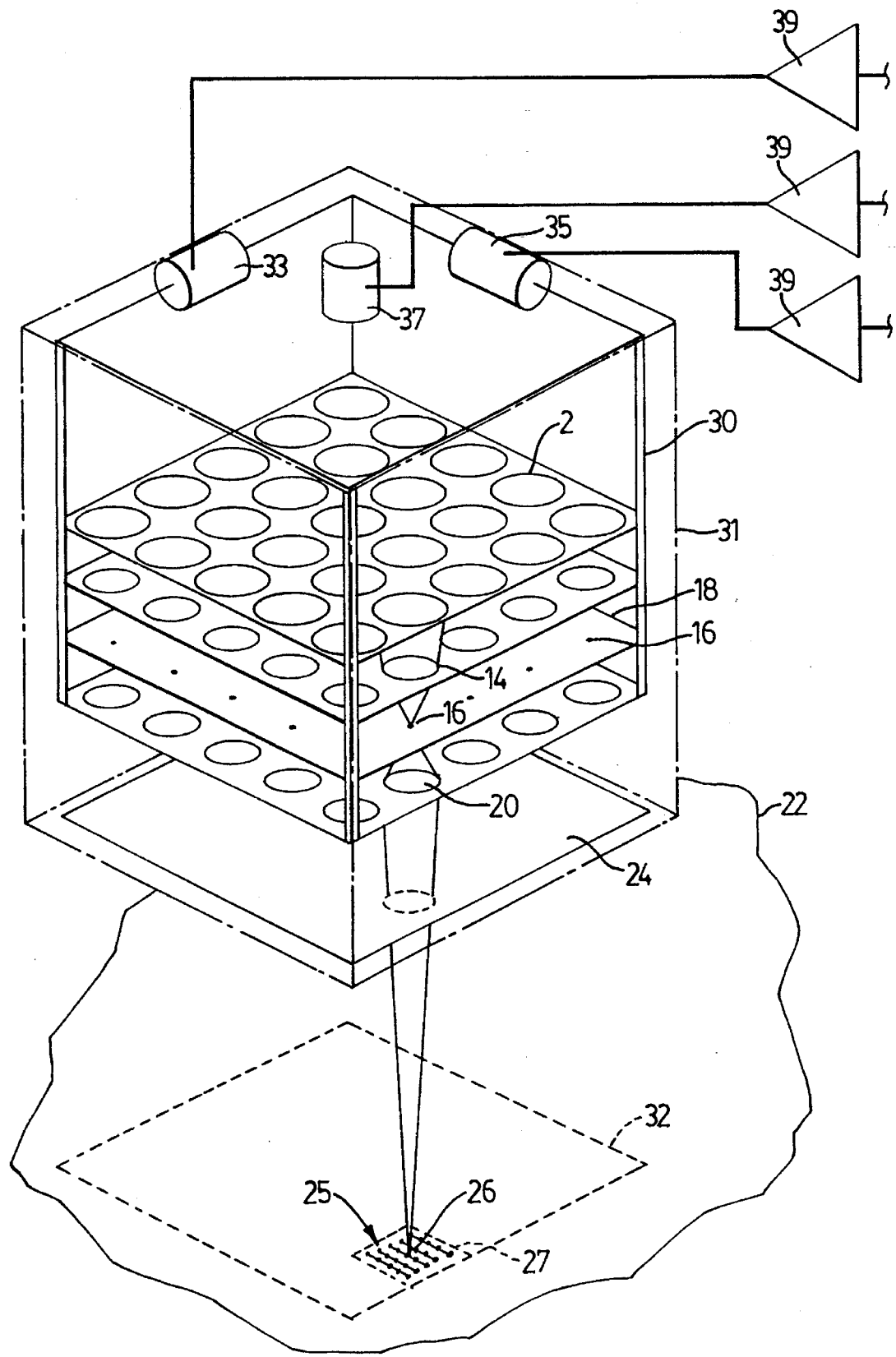
FIG. 2 shows diagrammatically an imaging device including an array of such scanning devices.

An image of body tissue 22 or other acoustically transmissive material is generated in stages using the apparatus of FIG. 2. First, in a translational stage, the scanning array 30 is moved in small steps (a fraction of the spacing of the axes of the focusing systems in the arrays) in its own plane between each pulse. At each step the acoustic transducers 2 individually generate a brief coherent pulse of ultrasonic energy at a predetermined frequency which is focused by the lens system to a point within the body 22. The translational motion, over an area shown in FIG. 1 at 32, is preferably in a "dither" pattern 25 designed so that the systems in the array will together completely map the tissue in the image plane at a desired lateral resolution, with each system mapping an area 27 determined by the pitch of the array. In the next stage, the scanning array is advanced incrementally in a direction perpendicular to the acoustic axes of the focusing systems, and a further translational stage follows in order to map an adjacent parallel image plane of the tissue. In this manner successive layers of the tissue, each with an area equal to that of the scanning array, are imaged at lateral and axial resolutions corresponding to the dither increment and the perpendicular advance increment. The signals received by the individual acoustic transducers of the scanning array are discriminated from each other by the confocal nature of the ultrasonic transducer lens system which has the effect of increasing lateral and axial resolution while limiting out-of-focus noise. In addition, by time-of-flight techniques involving only accepting received signals during a temporal window commensurate with the expected arrival time of a return signal, extraneous signals and cross-talk between the acoustic elements of the array can be further reduced. By monitoring frequency shifts of the received signals, provision can be made for the use of doppler techniques to study fluid flow within tissue, and different ultrasonic frequencies may be utilized to obtain optimal discrimination of tissue types. Through computer processing the data developed during dithering of individual devices within the array can be rearranged and displayed utilizing a conventional raster-type scan, allowing tomographic images to be regenerated using existing imaging software. These and other known computational procedures may be utilized to enhance and assemble the images into a three-dimensional volume for clinical viewing.

The total time for a complete tissue scan is significantly reduced by the scanning array system. If, for example the array 30 consists of 8×10 devices with centres 1 cm apart, there are 25 steps in the dither pattern, and there are 50 translational increments perpendicular to the acoustic axes of the scanning array of 0.2 cm, then an image of a tissue volume of 8 cm×10 cm×10 cm at a volume resolution of 0.008 cm$^3$ is produced. If the time for an acoustic pulse to be sent and received and for the translational actuators to move the scanning array through one dither increment is approximately 1 ms, the entire volume can be imaged in about 1.25 seconds. This rapid processing rate makes it feasible to utilize images generated by the system to guide the insertion of surgical instruments such as biopsy needles.

Figure 3:
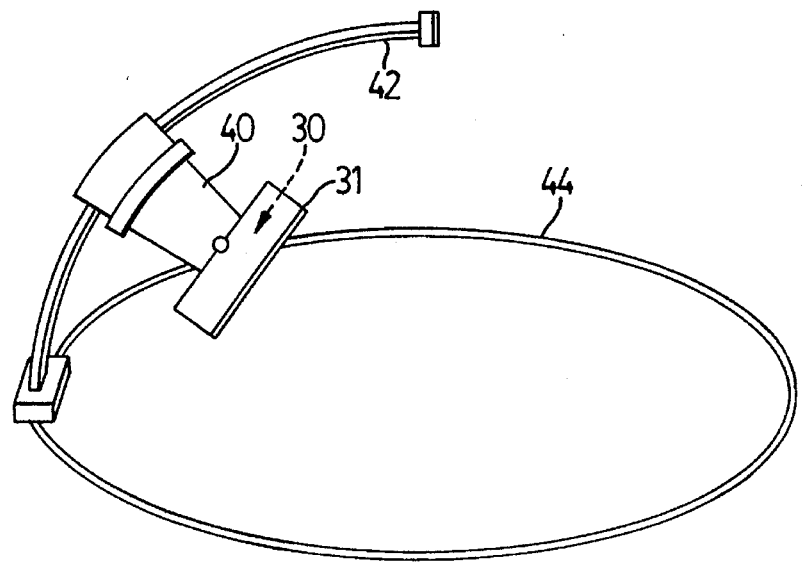
FIGS. 3 and 4 show diagrammatically how the imaging device according to claim 2 may be utilized tomographic imaging.
Figure 4:
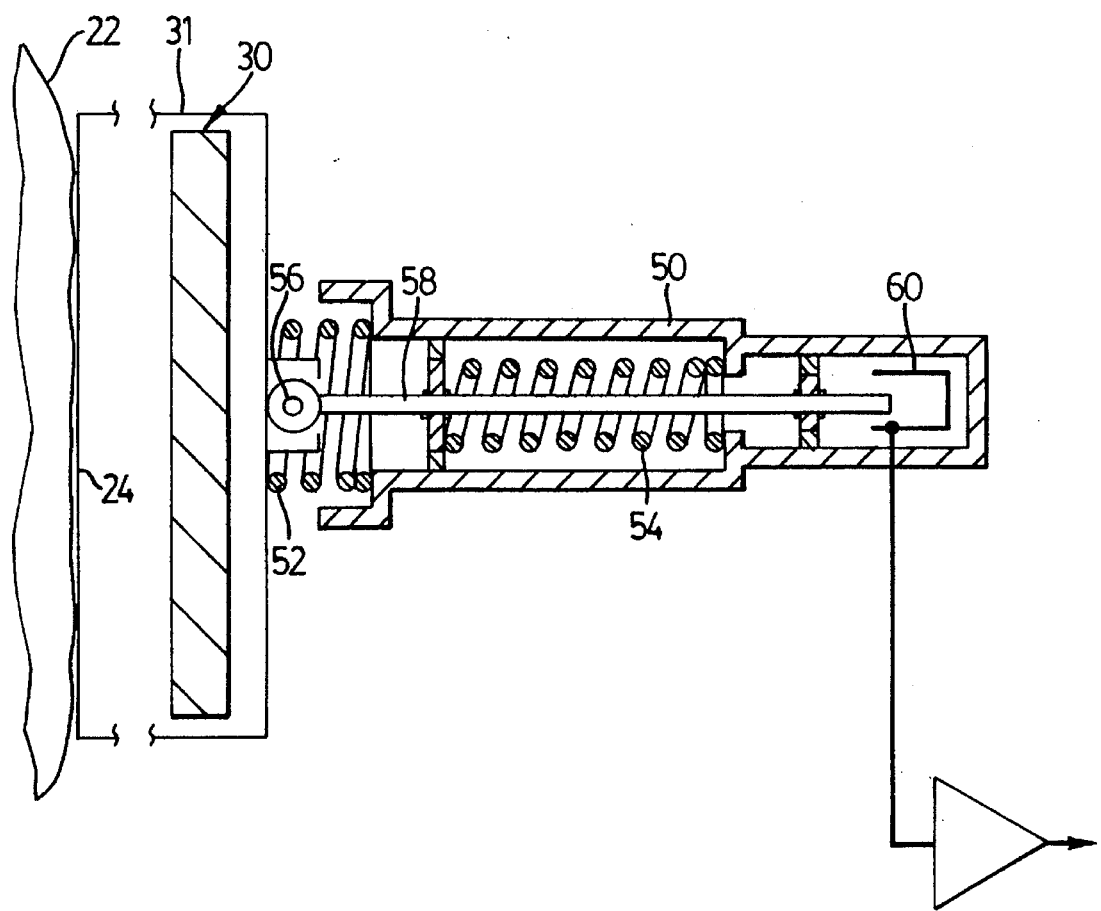

FIGS. 3 and 4 illustrate two ways in which the scanning array described above can be applied. In FIG. 3, the array 30 is mounted on a spring-loaded extensible strut 40 in turn movable around a quadrant 42 itself mounted at one end to a circular track 44. By including suitable actuators and displacement transducers in the various mountings, the housing 31 of the array 30 can be accurately positioned within a hemispherical volume under control of the control unit 6. Thus a pressure-sensitive sensor incorporated in a continuous or discrete feedback system controls the extension of the strut 40 to maintain a fixed position on the surface of the tissue to be imaged. The entire device is then stepped over the surface of the tissue to be imaged in a hemispherical envelope with the step size equal to the width of the scanning array 30, which performs a scan at each step. The transducers provide data to locate the position of the array and its orientation precisely so that a three-dimensional image of the tissue can be built up without distortion by combining images formed at each step.

In FIG. 4, the scanning array 30 is shown mounted to a hand-held support 50. An operator uses the support to bring the coupling membrane 24 to the surface of the tissue being imaged and holds it there while the scanning array completes its tomographic scan. Springs 52 and 54 act to press the array, universally mounted by a ball and socket joint 56 on a rod 58 journalled within the support 50, and a sensor 60 coacting with the rod determines when appropriate pressure has been applied to the array by the operator so as to enable scanning.

Although the resolution of conventional ultrasonic imaging systems is related to the frequency utilized, and pulse width, the essentially echographic nature of such systems typically limits their lateral resolution to about 5 millimeters, whereas using the confocal principles of the present invention, lateral resolutions which are reduced by an order of magnitude should be obtainable, thus enabling recognition of much smaller features, and rendering ultrasonic techniques suitable for mammography. Transducers may be fabricated from machinable piezo-ceramics, but preferably piezoelectric plastics are utilized since these are particularly well adapted to the fabrication of arrays. Similarly, the acoustic lens and pin-hole arrays utilized are readily fabricated as plastic mouldings which are of relatively low mass and thus permit the array to be stepped rapidly within its casing by voice-coil or other suitable actuators capable of rapid stepping rates. An exemplary transducer element within the array may have a diameter of about 10 mm, and operate at a frequency of 20 MHz, and a power density of more than about 50 mW/cm$^2$, so as to avoid any risk of excessive power dissipation in tissue being examined.

Although the embodiment described uses the same transducers to both transmit and receive acoustic energy, a separate transmitter or transmitters could be utilized to insonify the tissue to be scanned, but there would be significant loss of the advantages of the confocal arrangement since the transmitted energy would not be concentrated at the focal points of the confocal focusing systems, thus reducing the intensity of the reflected signals and increasing background noise. The dithering motion of the array during scanning could be continuous, since displacement of the points of focus during actual reflection of a pulse will not usually be significant. It would also be possible to displace only parts of the focusing system during dithering, or to cause relative displacement of the parts, in order to provide a desired shift in the point of focus. For example, it may be possible in some cases to move only the second stage lenses or the aperture plate provided that a uniform level of insonification of the points of focus can be maintained.

I claim:

1. An ultrasonic imaging device comprising at least one acoustic transducer with a confocal acoustic focusing system, and means to move the point of focus of each system progressively to different coordinates within an acoustically transmissive volume to gather data as to the acoustic reflectivity of matter within said volume at said different coordinates, and means to construct an image or images of the volume from said data.

2. A device according to claim 1, wherein multiple transducers and confocal focusing systems are disposed in an array.

3. A device according to claim 2, wherein the array is a two-dimensional planar array.

4. A device according to claim 3, wherein the means to move the points of focus includes actuators to move the array on two perpendicular axes parallel to the plane of the array and a third axis perpendicular to the plane of the array.

5. A device according to claim 4, wherein the actuators moving the array in its plane do so in a dither pattern of dimensions in accordance with the spacing of the axes of the focusing systems in the array.

6. A device according to claim 1, wherein each transducer is an electroacoustic transducer connected to a driver for applying pulses of electrical energy at an ultrasonic frequency to the transducer to cause it to transmit pulses of acoustic energy, and to a preamplifier for receiving from the transducer electrical energy at the same frequency resulting from reflected acoustic energy received by the transducer.

7. A device according to claim 1, wherein each confocal acoustic focusing system includes a first acoustic lens associated with the transducer, an aperture plate having a pinhole upon which the first lens is focused, and a second acoustic lens on an opposite side of the aperture plate to the first lens and focused upon said pin-hole and said point of focus respectively.

8. A device according to claim 1, including a membrane providing a coupling layer between said at least one focusing system and said volume to be imaged.

* * * * *